United States Patent
Takahashi et al.

(10) Patent No.: US 11,938,346 B2
(45) Date of Patent: Mar. 26, 2024

(54) PARTICLE BEAM THERAPY APPARATUS AND CONTROL METHOD THEREOF

(71) Applicant: Hitachi, Ltd., Tokyo (JP)

(72) Inventors: Hiroki Takahashi, Tokyo (JP); Masanori Suzuki, Tokyo (JP); Takuto Yagihashi, Tokyo (JP); Takeshi Fujita, Tokyo (JP); Isao Furuse, Tokyo (JP); Yuko Okada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 435 days.

(21) Appl. No.: 17/287,237

(22) PCT Filed: Oct. 16, 2019

(86) PCT No.: PCT/JP2019/040569
§ 371 (c)(1),
(2) Date: Apr. 21, 2021

(87) PCT Pub. No.: WO2020/105320
PCT Pub. Date: May 28, 2020

(65) Prior Publication Data
US 2021/0379402 A1 Dec. 9, 2021

(30) Foreign Application Priority Data
Nov. 20, 2018 (JP) .................. 2018-217424

(51) Int. Cl.
*A61N 5/10* (2006.01)
(52) U.S. Cl.
CPC ........... *A61N 5/107* (2013.01); *A61N 5/1049* (2013.01); *A61N 5/1083* (2013.01); *A61N 2005/1087* (2013.01)
(58) Field of Classification Search
None
See application file for complete search history.

(56) References Cited

U.S. PATENT DOCUMENTS

| | | | |
|---|---|---|---|
| 8,467,497 B2* | 6/2013 | Lu .................. | A61N 5/1049 378/65 |
| 8,509,383 B2* | 8/2013 | Lu .................. | A61N 5/1049 378/65 |

(Continued)

FOREIGN PATENT DOCUMENTS

| | | |
|---|---|---|
| JP | 2014-23741 A | 2/2014 |
| JP | 2016-15299 A | 8/2016 |

(Continued)

OTHER PUBLICATIONS

International Search Report of PCT/JP2019/040569.
Chinese Office Action received in corresponding Chinese Application No. 201980063115.6 dated Aug. 26, 2022.

*Primary Examiner* — David P Porta
*Assistant Examiner* — Djura Malevic
(74) *Attorney, Agent, or Firm* — MATTINGLY & MALUR, PC

(57) ABSTRACT

A particle beam therapy apparatus has a position and posture setter that moves a movable body, that is at least one of the irradiation nozzle and the treatment table. A movement path of the movable body is determined when adapting the positional posture of the movable body from one condition among a plurality of prescribed conditions to another condition. An evaluation value is obtained for adapting the positional posture of the movable body to each of a plurality of prescribed conditions. This evaluation value is for a case of moving the movable body according to the movement path. A setting order is determined for adapting the positional posture of the movable body to each prescribed condition based on the evaluation value; and the positional posture of the movable body is adapted to each of the plurality of prescribed conditions by moving the movable body according to the determined movement path.

13 Claims, 13 Drawing Sheets

(56) References Cited

U.S. PATENT DOCUMENTS

| | | | |
|---|---|---|---|
| 9,630,026 B2* | 4/2017 | Froehlich | A61N 5/1082 |
| 10,039,937 B2* | 8/2018 | Tachikawa | A61N 5/1048 |
| 10,052,501 B2* | 8/2018 | Froehlich | A61N 5/103 |
| 10,272,264 B2* | 4/2019 | Ollila | A61N 5/1039 |
| 10,307,615 B2* | 6/2019 | Ollila | A61N 5/1039 |
| 10,549,115 B2* | 2/2020 | Papp | A61N 5/1047 |
| 10,821,301 B2* | 11/2020 | Nishio | A61B 6/5247 |
| 11,179,129 B2* | 11/2021 | Harrington | A61B 6/5217 |
| 11,285,339 B2* | 3/2022 | Ollila | A61N 5/1045 |
| 11,491,349 B2* | 11/2022 | Marash | A61N 5/1049 |
| 2009/0116616 A1* | 5/2009 | Lu | A61N 5/1049 378/65 |
| 2009/0252291 A1* | 10/2009 | Lu | A61N 5/1049 378/65 |
| 2013/0131430 A1* | 5/2013 | Froehlich | A61N 5/1042 600/1 |
| 2015/0265855 A1* | 9/2015 | Tachikawa | A61N 5/1048 600/1 |
| 2016/0155228 A1* | 6/2016 | Sakata | G06T 11/008 382/132 |
| 2017/0173366 A1* | 6/2017 | Froehlich | A61N 5/10 |
| 2017/0216622 A1* | 8/2017 | Fujitaka | A61N 5/103 |
| 2018/0021594 A1* | 1/2018 | Papp | A61N 5/103 600/1 |
| 2018/0078789 A1* | 3/2018 | Ollila | A61N 5/1042 |
| 2018/0160994 A1* | 6/2018 | Harrington | A61B 6/5217 |
| 2019/0060672 A1* | 2/2019 | Takahashi | A61B 6/487 |
| 2019/0209863 A1* | 7/2019 | Ollila | A61N 5/1031 |
| 2019/0308033 A1* | 10/2019 | Nishio | A61N 5/1049 |
| 2021/0379402 A1* | 12/2021 | Takahashi | A61N 5/1049 |
| 2022/0176160 A1* | 6/2022 | Ollila | A61N 5/1039 |

FOREIGN PATENT DOCUMENTS

| | | |
|---|---|---|
| JP | 2016-152992 A | 8/2016 |
| JP | 2017-64505 W | 4/2017 |
| JP | 2017-131399 A | 8/2017 |

* cited by examiner

[FIG. 1]
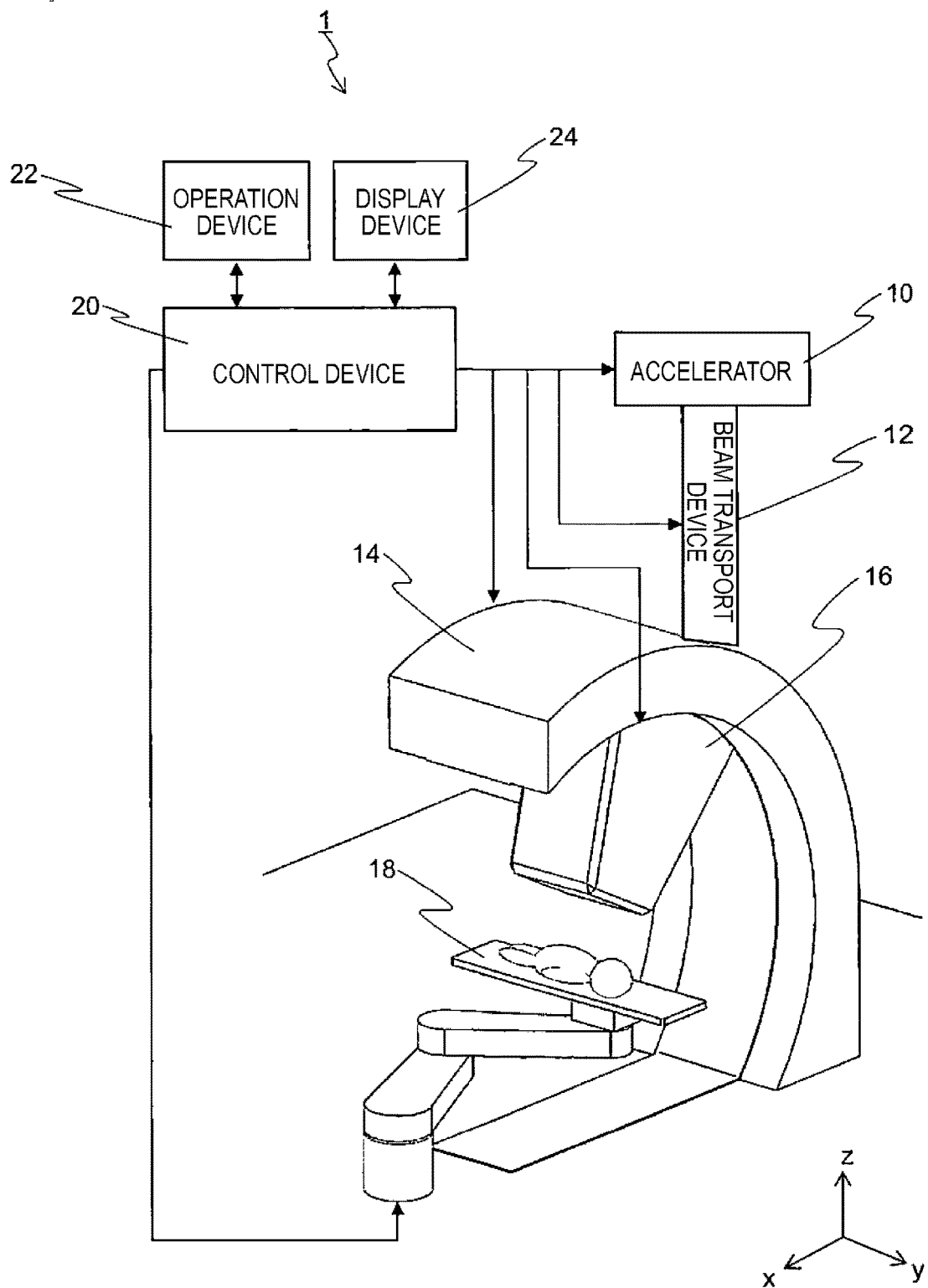

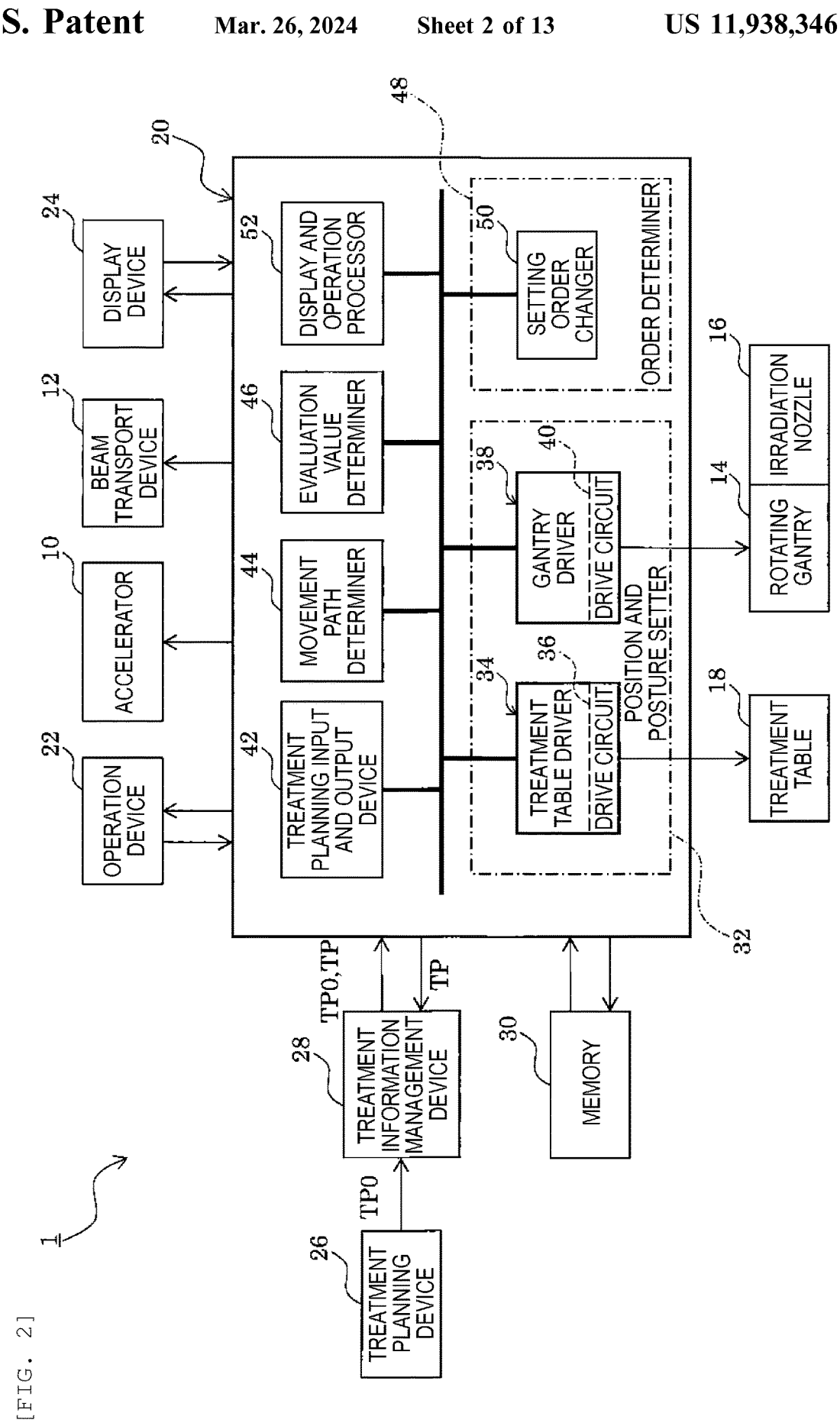
[FIG. 2]

[FIG. 3]
| # | PRESCRIBED CONDITION | ROTATING GANTRY | TREATMENT TABLE |
|---|---|---|---|
| 1 | Stp 1<br>Tx 1 | 30° | 270° |
| 2 | Stp 2<br>Tx 2 | 90° | 250° |
| 3 | Stp 3<br>Tx 3 | 155° | 0° |
| 4 | Stp 4<br>Tx 4 | 40° | 180° |
|  |  |  |  |
[FIG. 4]
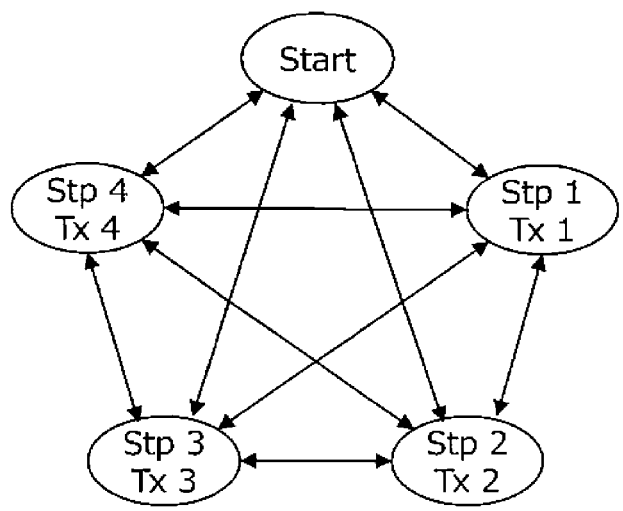
[FIG. 5]
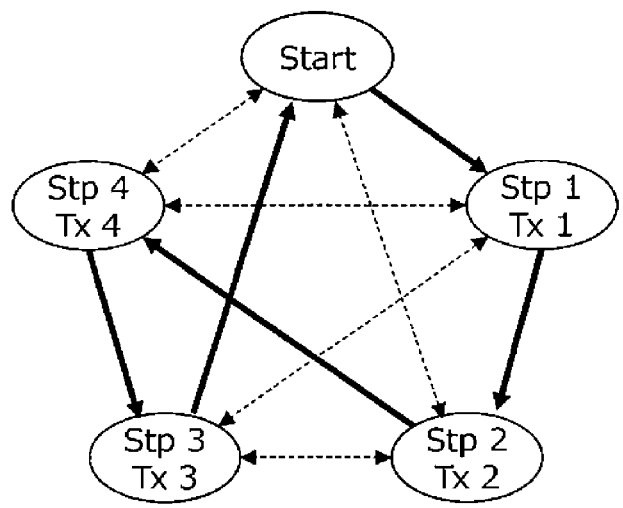

[FIG. 6]

| # | PRESCRIBED CONDITION | ROTATING GANTRY | TREATMENT TABLE | EDITING |
|---|---|---|---|---|
| 1 | Stp 1<br>Tx 1 | 30° | 270° | ▨ |
| 2 | Stp 2<br>Tx 2 | 90° | 250° | ▨ |
| 3 | Stp 4<br>Tx 4 | 40° | 180° | ▨ |
| 4 | Stp 3<br>Tx 3 | 155° | 0° | ▨ |
|   |   |   |   |   |

MOVEMENT TIME : ○○ min

[FIG. 7]

| # | PRESCRIBED CONDITION | ROTATING GANTRY | TREATMENT TABLE | EDITING |
|---|---|---|---|---|
| 1 | Stp 1 Tx 1 | 30° | 270° | ▨ |
| 3 | Stp 4 | | | |
| 2 | Stp 2 Tx 2 | 90° | 250° | ▨ |
| 4 | Tx 3 | 155° | 0 | ▨ |

MOVEMENT TIME : ◯◯ min

↓

| # | PRESCRIBED CONDITION | ROTATING GANTRY | TREATMENT TABLE | EDITING |
|---|---|---|---|---|
| 1 | Stp 1 Tx 1 | 30° | 270° | ▨ |
| 2 | Stp 4 Tx 4 | 40° | 180° | ▨ |
| 3 | Stp 2 Tx 2 | 90° | 250° | ▨ |
| 4 | Stp 3 Tx 3 | 155° | 0° | ▨ |

MOVEMENT TIME : △△ min

[FIG. 8]
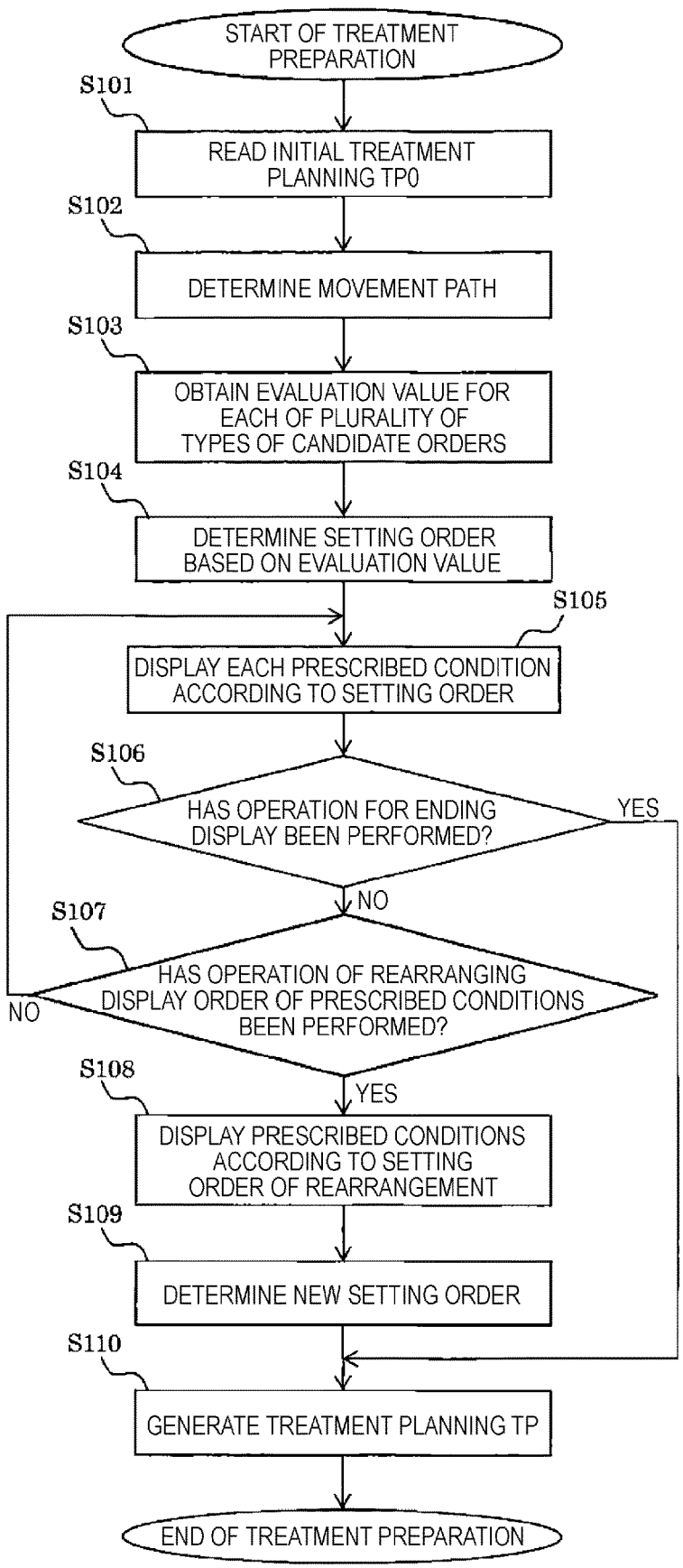

[FIG. 9]
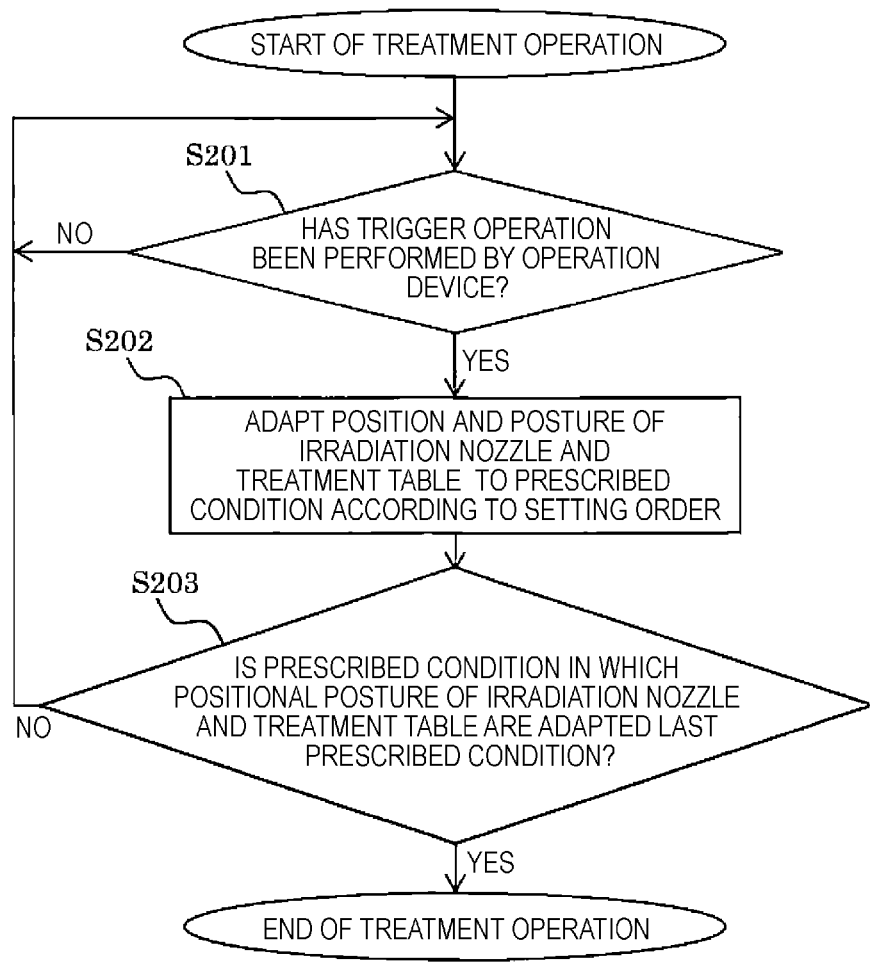

[FIG. 10]
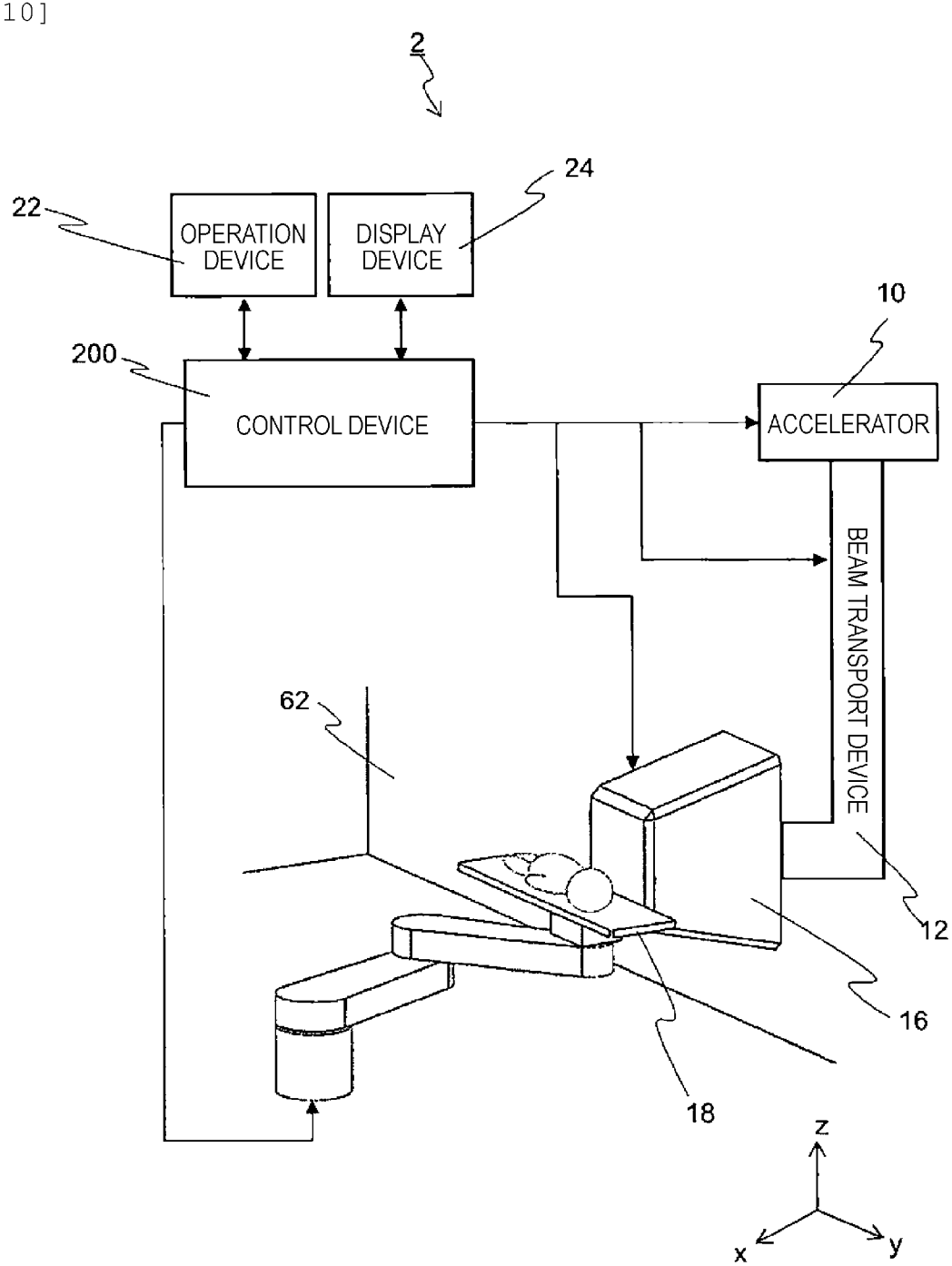

[FIG. 11]
| # | PRESCRIBED CONDITION | ROTATING GANTRY | TREATMENT TABLE |
|---|---|---|---|
| 1 | Stp 1 | 0° | 270° |
| 2 | Tx 1 | 180° | 180° |
| 3 | Tx 2 | 60° | 0° |
| 4 | Tx 3 | 90° | 180° |
|   |   |   |   |
[FIG. 12]
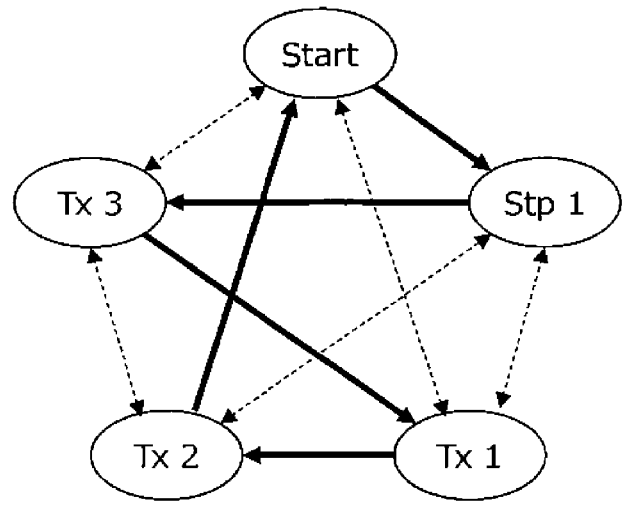

[FIG. 13]
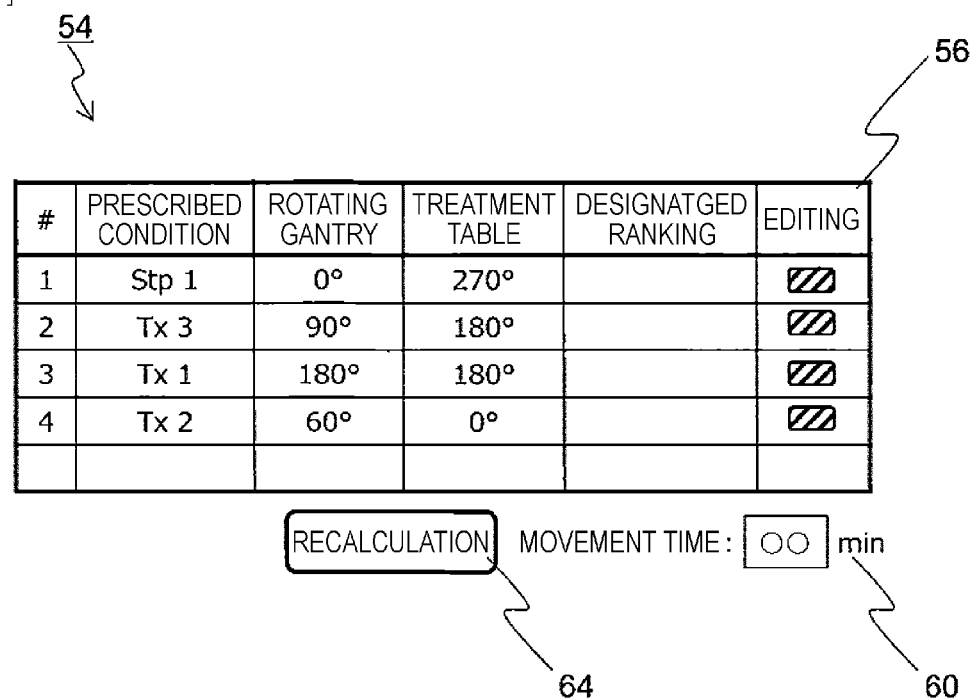

[FIG. 14]
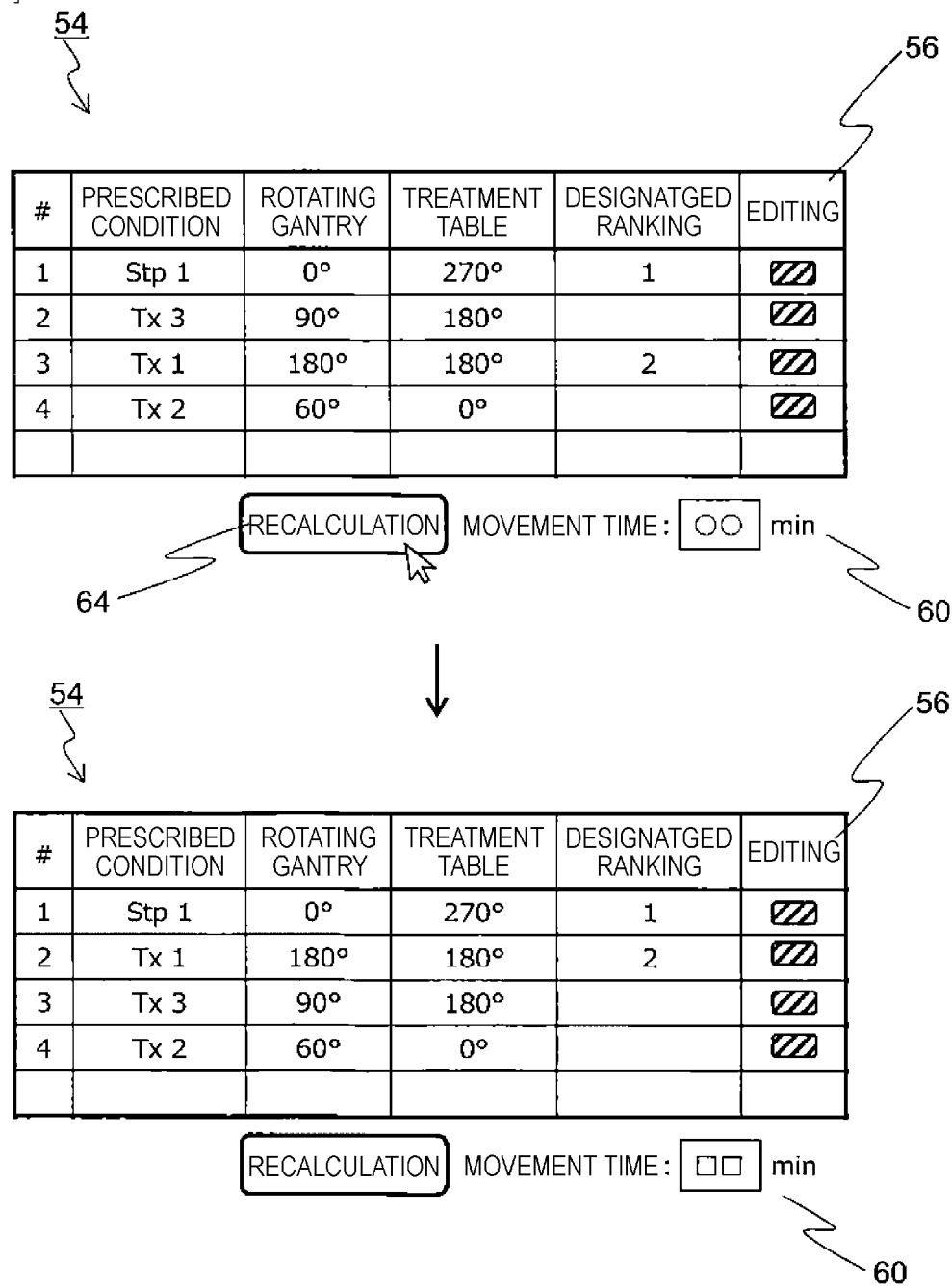

[FIG. 15]
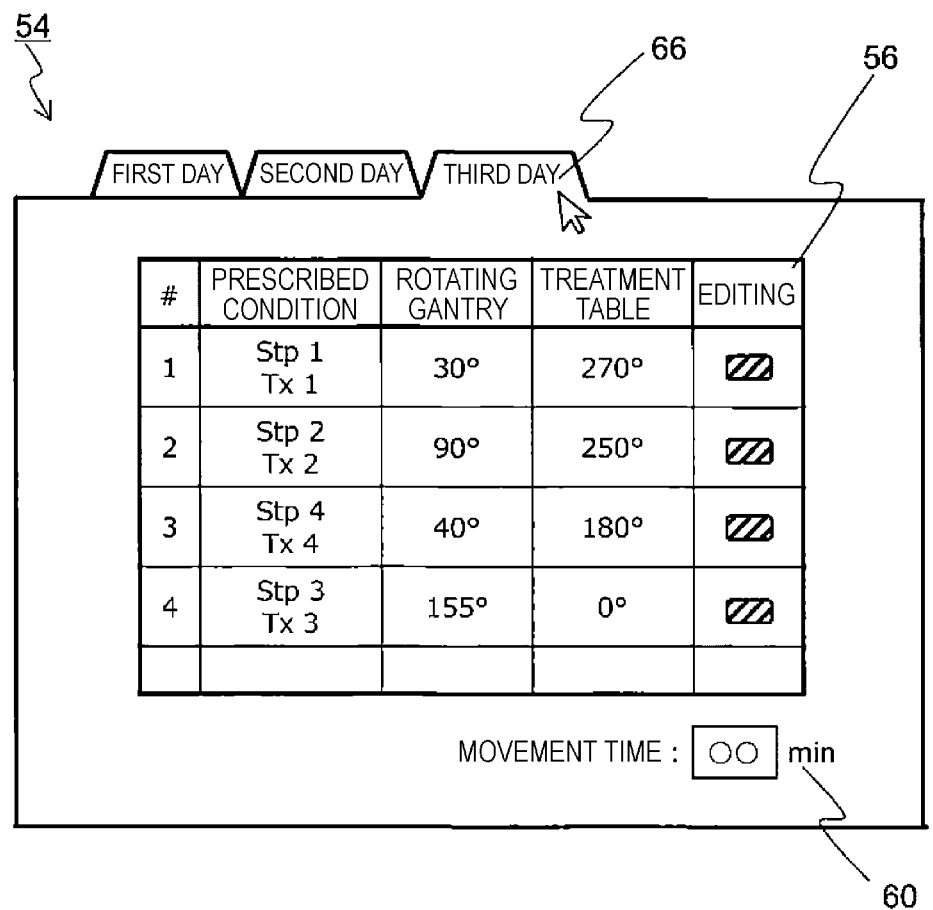

[FIG. 16]
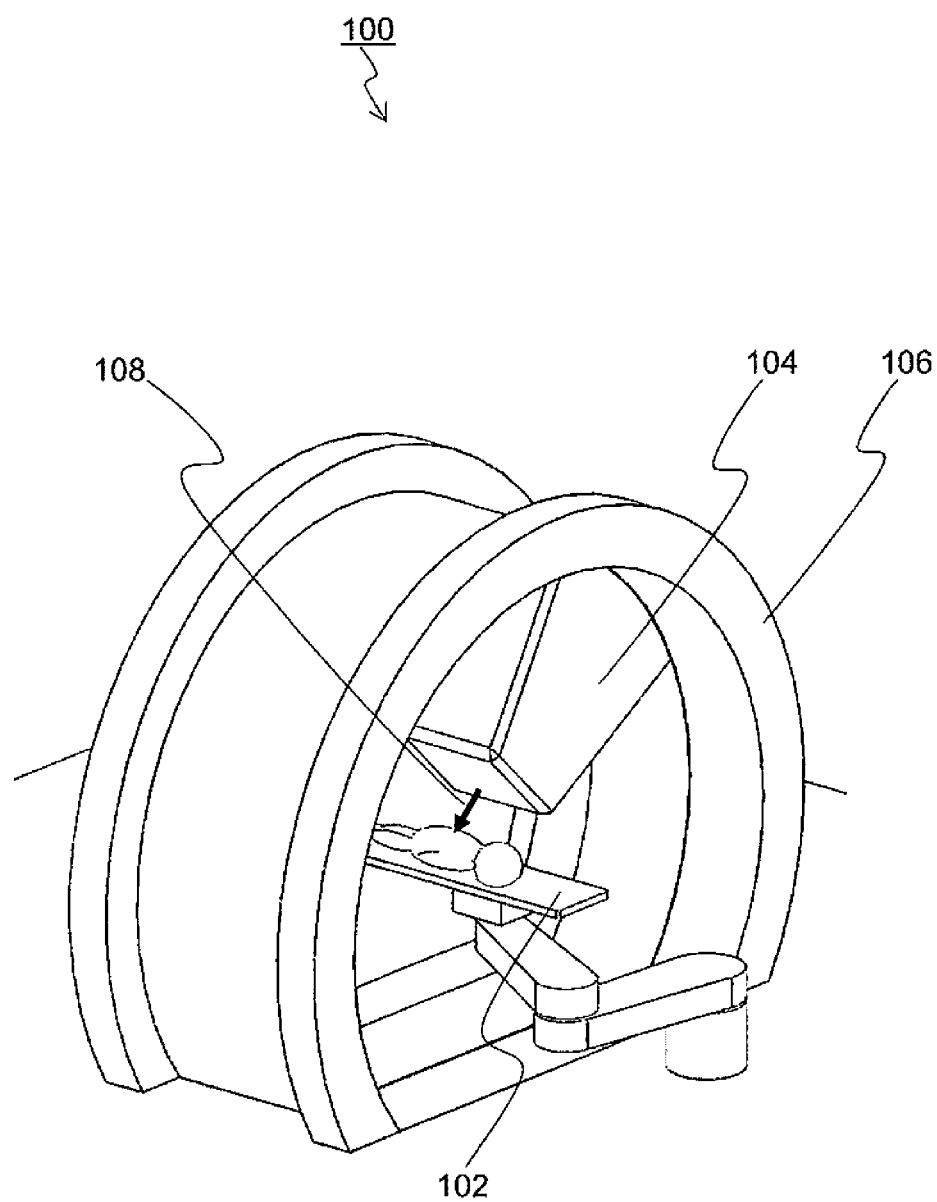

PARTICLE BEAM THERAPY APPARATUS AND CONTROL METHOD THEREOF

TECHNICAL FIELD

The present invention relates to a particle beam therapy apparatus and a control method thereof, and more particularly to a technique for setting a position or posture of an irradiation nozzle or treatment table.

BACKGROUND ART

In cancer treatment, a particle beam therapy that irradiates an affected area with particle beams such as proton beams and carbon ion beams has been attracting attention in recent years. In FIG. 16, a general particle beam therapy apparatus 100 is schematically illustrated. In the particle beam therapy apparatus 100, an affected area is irradiated with a particle beam 108 based on particles, which are accelerated by an accelerator until the particles have the required energy, from an irradiation nozzle 104.

In order to irradiate the affected area with the particle beam 108 while avoiding normal tissue, the particle beam therapy apparatus 100 includes a mechanism for irradiating the affected area with the particle beam 108 from various directions. That is, the particle beam therapy apparatus 100 includes the irradiation nozzle 104 that is moved in an arc shape by a rotating gantry 106, and a treatment table 102 whose a position and posture are adjustable. By an action of the rotating gantry 106 and an action of the treatment table 102 on which the patient is placed, the affected area is irradiated with the particle beam 108 from various directions.

JP-A-2014-23741 (PTL 1) describes a technique for determining irradiation conditions in radiation therapy as a technique related to the present invention. PTL 1 describes conditions relating to a radiation beam that prescribes the irradiation intensity and irradiation direction as the irradiation conditions.

CITATION LIST

Patent Literature

PTL 1: JP-A-2014-23741

SUMMARY OF INVENTION

Technical Problem

In the treatment using the particle beam therapy apparatus, data called treatment planning is created in advance. The treatment planning defines a plurality of prescribed conditions for the irradiation nozzle and treatment table. Each prescribed condition defines, for example, the position or posture of the irradiation nozzle and the treatment table. In one type of treatment, the plurality of prescribed conditions are sequentially applied to the irradiation nozzle and the treatment table one by one. With this configuration, the irradiation nozzle and the treatment table are sequentially set to positions and postures determined by each prescribed condition. Each time one prescribed condition is applied to the irradiation nozzle and the treatment table, medical treatment such as irradiation of the affected area with the particle beam is performed.

In general, in the treatment planning, the order in which the plurality of prescribed conditions are applied to the irradiation nozzle and the treatment table is not defined. For that reason, an operator empirically determines an application order of the plurality of prescribed conditions while referring to the treatment planning. In the technical field of particle beam therapy, it is desired to reduce a burden on such an operator.

An object of the present invention is to reduce the burden on the operator of the particle beam therapy apparatus.

Solution to Problem

A particle beam therapy apparatus according to an embodiment of the present invention includes an irradiation nozzle that irradiates a particle beam, a treatment table on which a patient is placed, and a control device that moves a movable body and sets a relative position and posture of the irradiation nozzle and the treatment table, the movable body being at least one of the irradiation nozzle and the treatment table that is capable of motion, and in which the control device determines a movement path of the movable body when adapting the positional posture of the movable body from one condition among a plurality of prescribed conditions to another condition, obtains an evaluation value for a case of adapting the positional posture of the movable to each of a plurality of prescribed conditions, the evaluation value representing a motion state of the moving body when one type of treatment is performed by moving the moving body according to the movement path, determines a setting order for adapting the position and posture of the movable body to each of the plurality of prescribed conditions based on the evaluation value, and adapts the positional posture of the movable body from one condition among the plurality of prescribed conditions to another condition by moving the movable body according to the movement path.

Advantageous Effects of Invention

According to the present invention, the burden on the operator of the particle beam therapy apparatus is reduced.

BRIEF DESCRIPTION OF DRAWINGS

FIG. 1 is a diagram schematically illustrating a particle beam therapy apparatus according to a first embodiment.

FIG. 2 is a diagram illustrating a specific configuration of the particle beam therapy apparatus.

FIG. 3 is a table illustrating an example of prescribed conditions defined by initial treatment planning.

FIG. 4 is a diagram conceptually illustrating five prescribed conditions.

FIG. 5 is a diagram conceptually illustrating a setting order in which a movement time is minimized.

FIG. 6 is a table illustrating an example of an image displayed on a display device.

FIG. 7 is a diagram illustrating an operation of changing a setting order.

FIG. 8 is a flowchart illustrating a flow of preparation for treatment.

FIG. 9 is a flowchart of a treatment action executed by a control device.

FIG. 10 is a diagram schematically illustrating a particle beam therapy apparatus according to a second embodiment.

FIG. 11 is a table illustrating an example of the prescribed conditions defined by the initial treatment planning.

FIG. 12 is a diagram conceptually illustrating the setting order in which the movement time is minimized.

FIG. 13 is a table illustrating an example of an image displayed on the display device.

FIG. 14 is a diagram illustrating an operation of changing the setting order by inputting designated ranking.

FIG. 15 is a diagram illustrating another image displayed on the display device.

FIG. 16 is a diagram schematically illustrating a general particle beam therapy apparatus.

DESCRIPTION OF EMBODIMENTS

A particle beam therapy apparatus according to each embodiment of the present invention will be described below with reference to each drawing. The same items illustrated in a plurality of drawings are denoted by the same reference numerals, and a duplicate explanation thereof is avoided.

(1) Configuration of Particle Beam Therapy Apparatus

In FIG. 1, a particle beam therapy apparatus 1 according to a first embodiment of the present invention is schematically illustrated. In FIG. 1, an upward direction is defined as a z-axis positive direction when viewed from an operator. A direction in which a region surrounded by a rotating gantry 14 extends from the back side to the front side is defined as a y-axis positive direction. Furthermore, an x-axis is defined as a coordinate axis perpendicular to the z-axis and the y-axis.

The particle beam therapy apparatus 1 is an apparatus that irradiates an affected area with a particle beam of a heavy particle such as a proton and a carbon ion. The particle beam therapy apparatus 1 includes an accelerator 10, a beam transport device 12, the rotating gantry 14, an irradiation nozzle 16, a treatment table 18, a control device 20, an operation device 22, and a display device 24.

The particle beam therapy apparatus 1 generates the particle beam by the accelerator 10, the beam transport device 12, and the irradiation nozzle 16. The accelerator 10 may be provided in a room separate from a treatment room. The accelerator 10 may be an accelerator such as a synchrotron type accelerator or a cyclotron type accelerator. The accelerator 10 accelerates a particle until the particles have required energy. The beam transport device 12 guides the particle beam obtained by the accelerator 10 to the irradiation nozzle 16. The irradiation nozzle 16 irradiates the particle beam guided by the beam transport device 12.

The rotating gantry 14 moves the irradiation nozzle 16 over an arc-shaped section extending from the bottom to the top. With this configuration, a rotation angle position of the irradiation nozzle 16 is freely adjustable. The rotation angle position is defined as an angle indicating the direction viewed from a reference point located at a position surrounded by the rotating gantry 14. By adjusting the rotation angle position of the irradiation nozzle 16, the direction of the particle beam irradiated from the irradiation nozzle 16 is adjusted. Here, an example of the reference point is an isocenter or a rotation center of the rotating gantry. Ideally, the center of rotation of the rotating gantry and the mechanical isocenter are located approximately at the same position.

A patient is placed on the treatment table 18. The treatment table 18 is freely adjustable in position represented by xyz-coordinates. Furthermore, the treatment table 18 is freely adjustable in posture represented by a pitch angle, roll angle, and yaw angle. The yaw angle is defined as an angle around the z-axis of a leading axis that indicates the direction in which the patient's head is directed. The pitch angle is defined as an elevation angle of the leading axis with respect to the xy-plane. The roll angle is defined as a rotation angle around the leading axis. In the figure, a robot arm type treatment table is described as an example, but a treatment table including an x-axis drive mechanism, a y-axis drive mechanism, a z-axis drive mechanism, and a rotation mechanism that translate the top plate of the treatment table on each of the x-axis, y-axis, and z-axis may be used.

When treating a patient, the treatment table 18 is moved to a position surrounded by an arc-shaped section in which the irradiation nozzle 16 moves. By the action of the rotating gantry 14 and the treatment table 18, the rotation angle position of the irradiation nozzle 16 and the position and posture of the treatment table 18 are adjusted. With this configuration, the affected area can be irradiated with the particle beam from various directions.

The operation device 22 outputs operation information for controlling the particle beam therapy apparatus 1 to the control device 20 in response to an operation by the operator. The control device 20 controls actions of the accelerator 10, the beam transport device 12, the rotating gantry 14, and the treatment table 18. The display device 24 displays an image according to the action of the control device 20. The operation device 22 may be configured with a keyboard, a mouse, a touch pad, buttons, levers, and the like. The display device 24 may be a display device. The operation device 22 may be a touch panel incorporated in the display device 24.

In FIG. 2, a specific configuration of the particle beam therapy apparatus 1 is illustrated. The accelerator 10, the beam transport device 12, the rotating gantry 14, the treatment table 18, the operation device 22, and the display device 24 illustrated in FIG. 1 are connected to the control device 20. A treatment information management device 28 and a memory 30 are further connected to the control device 20. The treatment information management device 28 is connected to a treatment planning device 26, which is an external device.

The control device 20 includes a position and posture setter 32, a treatment planning input and output device 42, a movement path determiner 44, an evaluation value determiner 46, an order determiner 48, and a display and operation processor 52. The position and posture setter 32 includes a treatment table driver 34 and a gantry driver 38. The treatment table driver 34 includes a drive circuit 36 as an electric circuit for driving an actuator of the treatment table 18. The gantry driver 38 includes a drive circuit 40 as an electric circuit for driving the actuator of the rotating gantry 14.

Specific actions of components (position and posture setter 32, treatment planning input and output device 42, movement path determiner 44, evaluation value determiner 46, order determiner 48, and display and operation processor 52) included in the control device 20 will be described later.

Some or all of the plurality of components included in the control device 20 may be configured by a processor except for the drive circuits 36 and 40. The processor realizes each component by executing a program. This program may be stored in the memory 30 which serves as a storage medium. For the memory 30, for example, a storage device such as a hard disk, a USB memory, or an SD card is used. The memory 30 may be a storage on a communication line such as the Internet. One component included in the control device 20 may be configured with a plurality of processors that perform distributed processing.

Some or all of the plurality of components included in the control device 20 may be configured by an external computer except for the drive circuits 36 and 40. The external computer may be one which is directly connected to the control device 20 or connected to a communication line such as the Internet. One component included in the control device 20 may be configured with a plurality of external computers that perform distributed processing. Furthermore, some or all of the plurality of components included in the control device 20 may be individually configured by an electronic circuit as hardware.

For the treatment planning device 26, for example, an external computer connected to the treatment information management device 28 is used. The treatment information management device 28 may be connected to the treatment planning device 26 via a communication line such as the Internet.

(2) Prescribed Condition

The treatment planning device 26 transmits initial treatment planning TP0 to the treatment information management device 28 in advance. The initial treatment planning TP0 is initial information for the particle beam therapy apparatus 1 to perform a treatment action. The treatment information management device 28 stores the initial treatment planning TP0.

In the initial treatment planning TP0, a plurality of prescribed conditions that are applied to the irradiation nozzle 16 and the treatment table 18 when performing one type of treatment are defined. Each prescribed condition in this embodiment determines the rotation angle position of the irradiation nozzle 16 and the position and posture of the treatment table 18. In the following description, the rotation angle position of the irradiation nozzle 16 and the position and posture of the treatment table 18 are referred to as "positional posture of the irradiation nozzle 16 and the treatment table 18".

The prescribed conditions include a prescribed condition for setup and a prescribed condition for irradiation process. The setup is a step performed before irradiation of the particle beam. In the setup, for example, an X-ray image or a CT image around the affected area is captured. Then, based on the image obtained by image-capturing, the position of the patient is adjusted so that the position of the affected area during treatment and the isocenter match. By the prescribed condition for setup, the rotation angle position of the irradiation nozzle 16 and the position and posture of the treatment table 18 when aligning the affected area are determined.

The irradiation process is a process of irradiating the affected area with the particle beam. In general, in one type of treatment, the affected area is irradiated with the particle beams from a plurality of different directions, and irradiation is performed a plurality of times from one direction. For that reason, in the initial treatment planning TP0, prescribed conditions are defined at every plural irradiation. The rotation angle position of the irradiation nozzle 16 and the position and posture of the treatment table 18 during the irradiation process are determined by the prescribed condition for irradiation process.

In FIG. 3, an example of the prescribed conditions defined by the initial treatment planning TP0 is illustrated. The symbols "Stp1" to "Stp4" indicated in a "prescribed condition" field are symbols for distinguishing four prescribed conditions for setup. The symbols "Tx1" to "Tx4" indicated in the "prescribed condition" field are symbols for distinguishing four prescribed conditions for irradiation process. The numbers "1" to "4" in the field in which the symbol "#" is described indicate the order in which the positional posture of the irradiation nozzle 16 and the treatment table 18 is adapted to the respective prescribed conditions.

In FIG. 3, an example in which the rotation angle positions of the irradiation nozzle 16 are the same and the positions and postures of the treatment table 18 are the same for prescribed conditions Stpi and Txi (i is an integer of 1 to 4) is illustrated. Items corresponding to the prescribed conditions Stpi and Txi are indicated in a common field arranged horizontally.

In a "rotating gantry" field, the rotation angle position of the rotating gantry 14 is determined according to each prescribed condition. The rotation angle position of the rotating gantry 14 represents the rotation angle position of the irradiation nozzle 16. By prescribed conditions Stp1 and Tx1, the rotation angle position of the rotating gantry 14 is set to 30°. By prescribed conditions Stp2 and Tx2, the rotation angle position of the rotating gantry 14 is set to 90°. By prescribed conditions Stp3 and Tx3, the rotation angle position of the rotating gantry 14 is set to 155°. By prescribed conditions Stp4 and Tx4, the rotation angle position of the rotating gantry 14 is set to 40°.

In a "treatment table" field, the posture of the treatment table 18 is determined according to each prescribed condition. Each prescribed condition actually determines the position and posture of the treatment table 18. In FIG. 3, for simplicity of notation, only the yaw angle is illustrated as one geometric quantity representing the posture. When the yaw angle of the treatment table 18 is defined with the position of the affected area as the origin, a direction of arrival of the particle beam viewed from the affected area is represented by the rotation angle position of the irradiation nozzle 16 and the yaw angle of the treatment table 18. In this case, each prescribed condition illustrated in FIG. 3 can determine the irradiation direction of the particle beam to the affected area.

In the example illustrated in FIG. 3, the yaw angle of the treatment table 18 is set to 270° by the prescribed conditions Stp1 and Tx1. The yaw angle of the treatment table 18 is set to 250° by the prescribed conditions Stp2 and Tx2. The yaw angle of the treatment table 18 is set to 0° by the prescribed conditions Stp3 and Tx3. The yaw angle of the treatment table 18 is set to 180° by the prescribed conditions Stp4 and Tx4.

In FIG. 4, five prescribed conditions obtained by adding a start condition Start to the four prescribed conditions illustrated in FIG. 3 are conceptually illustrated. In the start condition Start, the rotation angle position of the irradiation nozzle 16 and the position and posture of the treatment table 18 when the patient gets on and off the treatment table 18 are defined. The double-headed arrow straight line connecting the prescribed conditions indicates that the positional posture of the irradiation nozzle 16 and the treatment table 18 can be transitioned between the prescribed conditions illustrated on both sides of the double-headed arrow straight line. In the example illustrated in FIG. 4, it is assumed that the patient gets on and off under the same conditions. The conditions for the patient to get on and off the treatment table 18 may be different.

(3) Process for Plurality of Prescribed Conditions (3-1) Movement Path

The process for a plurality of prescribed conditions as illustrated in FIG. 4 is described with reference to FIG. 2. The treatment planning input and output device 42 reads the initial treatment planning TP0 from the treatment information management device 28. The treatment planning input and output device 42 extracts information representing a plurality of prescribed conditions required for treatment from the initial treatment planning TP0.

The movement path determiner 44 determines the movement path of the treatment table 18 when adapting the position and posture of the treatment table 18 from one prescribed condition to another for any combination of selecting two from a plurality of prescribed conditions. That is, the movement path determiner 44 determines the movement path of the treatment table 18 between the plurality of prescribed conditions. Similarly, the movement path determiner 44 determines the movement path of the irradiation nozzle 16 between the plurality of prescribed conditions. In the example illustrated in FIGS. 3 and 4, the movement path determiner 44 determines the movement paths of the treatment table 18 and the irradiation nozzle 16 between the five prescribed conditions.

The movement path determiner 44 reads information related to a three-dimensional shape of the particle beam therapy apparatus 1 and information related to a size of the patient from the memory 30. The movement path determiner 44 determines the movement paths of the irradiation nozzle 16 and the treatment table 18 so that the irradiation nozzle 16 and the patient do not come into contact with each other, for example. The movement path determiner 44 may determine the movement paths of the irradiation nozzle 16 and the treatment table 18 so that the irradiation nozzle 16 and the treatment table 18 do not come into contact with each other. The movement path determiner 44 may determine a movement path so that apart other than the treatment table 18 of the particle beam therapy apparatus 1 and the patient or the parts of the particle beam therapy apparatus 1 do not collide with each other. The movement path determiner 44 determines the movement paths of the irradiation nozzle 16 and the treatment table 18 so that the irradiation nozzle 16 and the patient do not come into contact with each other and the irradiation nozzle 16 and the treatment table 18 do not come into contact with each other.

The movement of the treatment table 18 according to the movement path may be accompanied by motion in which the position of the treatment table 18 is constant and only the posture thereof changes. In this case, information representing the movement path also includes a geometric quantity (posture before change and posture after change) representing a change in the posture of the treatment table 18 when the position of the treatment table 18 is constant.

(3-2) Evaluation Value

In one type of treatment, the positional posture of the irradiation nozzle 16 and the treatment table 18 sequentially transitions according to each of the plurality of prescribed conditions. In the transition of the positional posture of the irradiation nozzle 16 and the treatment table 18, the irradiation nozzle 16 and the treatment table 18 move according to the movement path determined by the movement path determiner 44. The evaluation value determiner 46 obtains an evaluation value when one type of treatment is performed. The evaluation value is a value indicating a motion state of at least one of the irradiation nozzle 16 and the treatment table 18 when one type of treatment is performed.

The evaluation value includes, for example, the movement time of the irradiation nozzle 16 and the treatment table 18 when one type of treatment is performed. When the movement time of the irradiation nozzle 16 and the treatment table 18 is different, the longer of the movement time of the irradiation nozzle 16 and the treatment table 18 may be defined as the movement time of both the irradiation nozzle 16 and the treatment table 18. The movement time may include the time required for setup and irradiation process. The evaluation value may be work [J] given to the irradiation nozzle 16 and the treatment table 18 when one type of treatment is performed.

The evaluation value may be a value indicating a motion load given to the treatment table 18 when one type of treatment is performed. The motion load given to the treatment table 18 includes, for example, a movement distance and the movement time of the treatment table 18 when one type of treatment is performed. The motion load given to the treatment table 18 may be kinetic energy [J] given to the treatment table 18 when one type of treatment is performed, or a time-integrated value (momentum) [kg·m/s] of the force given to the treatment table 18.

(3-3) Setting Order

For one type of treatment, there are a plurality of types of candidates for the order in which the plurality of prescribed conditions are applied to the positional posture of the irradiation nozzle 16 and the treatment table 18. That is, for one type of treatment, there are a plurality of types of candidate orders that are candidates for the order in which the positional posture of the irradiation nozzle 16 and the treatment table 18 is sequentially adapted to a plurality of prescribed conditions.

The evaluation value determiner 46 obtains an evaluation value for each of the plurality of types of candidate orders. The order determiner 48 selects one of the plurality of types of candidate orders based on the evaluation value obtained for each of the plurality of types of candidate orders. The order determiner 48 determines one candidate order selected from the plurality of types of candidate orders as a setting order when actually performing one type of treatment.

When the evaluation value is a value indicating the movement time and movement distance of the irradiation nozzle 16 and the treatment table 18, or the work given to the irradiation nozzle 16 and the treatment table 18, the order determiner 48 may select the one having the smallest evaluation value among the plurality of candidate orders as the setting order. The order determiner 48 may randomly select one of the plurality of candidate orders whose evaluation value is less than a predetermined threshold value as the setting order.

Similarly, when the evaluation value indicates the motion load of the treatment table 18, the order determiner 48 may select the one having the smallest evaluation value among the plurality of candidate orders as the setting order. In this case as well, the order determiner 48 may randomly select one of the plurality of candidate orders whose evaluation value is less than the predetermined threshold value as the setting order.

In FIG. 5, the setting order in which the movement time as the evaluation value is minimized is conceptually illustrated. The order in which the positional posture of the irradiation nozzle 16 and the treatment table 18 (positional posture of control target) transitions is indicated by solid arrows as the setting order. In this setting order, firstly, the positional posture of the control target transitions from the positional posture adapted to the start condition Start to the positional posture adapted to the prescribed conditions Stp1 and Tx1. Secondly, the positional posture of the control target transitions from the positional posture adapted to the prescribed conditions Stp1 and Tx1 to the positional posture adapted to the prescribed conditions Stp2 and Tx2.

Thirdly, the positional posture of the control target transitions from the positional posture adapted to the prescribed conditions Stp2 and Tx2 to the positional posture adapted to the prescribed conditions Stp4 and Tx4. Fourthly, the positional posture of the control target transitions from the positional posture adapted to the prescribed conditions Stp4 and Tx4 to the positional posture adapted to the prescribed conditions Stp3 and Tx3. Fifthly, the positional posture of the control target transitions from the positional posture adapted to the prescribed conditions Stp3 and Tx3 to the positional posture adapted to the start condition Start.

(3-4) Display of Setting Order

The display and operation processor 52 displays each prescribed condition on the display device 24 in the setting order determined by the order determiner 48. In FIG. 6, an example of an image displayed on the display device 24 is illustrated. On a display screen 54, a setting order display unit 56 and an evaluation value display unit 60 are illustrated. On the setting order display unit 56, the contents of each prescribed condition are illustrated according to the setting order illustrated in FIG. 5.

The numerical values "1" to "4" in the field in which a symbol "#" is described indicate ranking of the prescribed conditions illustrated on the right side thereof. In this example, the ranking of the prescribed conditions Stp1 and Tx1 is the first, and the ranking of the prescribed conditions Stp2 and Tx2 is the second. The ranking of the prescribed conditions Stp4 and Tx4 is the third, and the ranking of the prescribed conditions Stp3 and Tx3 is the fourth.

Under the prescribed conditions Stpi and Txi (i is an integer of 1 to 4) indicated in the "prescribed condition" field, the rotation angle positions of the irradiation nozzle 16 are the same, and the positions and postures of the treatment table 18 are the same. In the field of "rotating gantry", the rotation angle positions of the rotating gantry 14 corresponding to the prescribed conditions Stpi and Txi are indicated. In the "treatment table" field, the yaw angles corresponding to the prescribed conditions Stpi and Txi are indicated.

In FIG. 6, the yaw angle is indicated as a representative value as one geometric quantity representing the posture in order to simplify the display. Regarding the treatment table 18, in addition to the yaw angle, an angle representing another posture may be indicated, or a position thereof may be indicated.

The specific numerical values of the rotation angle positions of the rotating gantry 14 associated with the respective prescribed conditions Stpi and Txi are the same as those in FIG. 3. The specific numerical values of the yaw angles of the treatment table 18 associated with the respective prescribed conditions Stpi and Txi are also the same as those in FIG. 3. On the evaluation value display unit 60, the movement time obtained for the set order being displayed is illustrated as an evaluation value.

In this way, on the display screen 54, the prescribed conditions are illustrated in an array according to the setting order. On the display screen 54, the setting order of each prescribed condition is indicated by a numerical value. That is, the display screen 54 illustrates information indicating the setting order of each prescribed condition.

(3-5) Change of Setting Order

The display and operation processor 52 displays an image corresponding to the operation performed in the operation device 22 on the display device 24. In FIG. 7, an operation for changing the setting order illustrated in the setting order display unit 56 is illustrated. As illustrated in the upper side of FIG. 7, a region where the symbol of the prescribed condition, the rotation angle position of the rotating gantry 14, and the yaw angle of the treatment table 18 are displayed is moved by dragging and dropping with a cursor. When dragging the region, an edit button 58 is pressed down by the cursor. When dropping the region, the edit button 58 is released from the cursor.

On the upper side of FIG. 7, the display screen 54 in which the region where the symbol of the prescribed condition, the rotation angle position of the rotating gantry 14, and the yaw angle of the treatment table 18 are indicated is moving is illustrated. On the lower side of FIG. 7, the display screen 54 after the movement of this region is illustrated. By this display action, the order in which the prescribed conditions are displayed is rearranged. On the evaluation value display unit 60 on the upper side of FIG. 7, the movement time before rearranging the setting order is illustrated. On the evaluation value display unit 60 on the lower side of FIG. 7, the movement time after rearranging the setting order is illustrated.

The rearrangement of the display order is performed by the operation device 22, the evaluation value determiner 46, a setting order changer 50, the display and operation processor 52, and the treatment planning input and output device 42. The setting order changer 50 recognizes the operation performed by the operation device 22 based on operation information read from the operation device 22. The setting order changer 50 determines a new setting order according to the rearrangement of the display order of the prescribed conditions. The evaluation value determiner 46 obtains an evaluation value for the new setting order. The display and operation processor 52 displays the evaluation value obtained for the new setting order on the display device 24.

The treatment planning input and output device 42 generates a treatment planning TP indicating a finally determined setting order, and transmits the treatment planning TP to the treatment information management device 28. The treatment information management device 28 stores the treatment planning TP.

In this way, in the process of changing the setting order, the setting order is displayed on the display screen 54, and the setting order changer 50 changes the setting order according to the operation information read from the operation device 22 and newly determines the setting order.

(3-6) Preparation for Treatment

In FIG. 8, a flowchart illustrating the flow of treatment preparation is illustrated. The process illustrated in this flowchart is executed by the control device 20. When the control device 20 includes a processor, each component configured inside the control device 20 executes the process illustrated in the flowchart of FIG. 8 by executing a program.

The treatment planning input and output device 42 reads the initial treatment planning TP0 from the treatment information management device 28 (S101). The treatment planning input and output device 42 extracts information indicating a plurality of prescribed conditions applied to one type of treatment from the initial treatment planning TP0.

The movement path determiner 44 determines the movement paths of the irradiation nozzle 16 and the treatment table 18 when the positional posture of the irradiation nozzle 16 and the treatment table 18 is adapted from one prescribed condition to another condition (S102). The movement path determiner 44 determines the movement paths between the plurality of prescribed conditions.

The evaluation value determiner 46 obtains an evaluation value for each of the plurality of types of candidate orders (S103). As described above, the candidate order is a candidate for the order in which the positional posture of the irradiation nozzle 16 and the treatment table 18 is sequentially adapted to the plurality of prescribed conditions.

The order determiner 48 selects one of the plurality of types of candidate orders based on the evaluation value obtained for each of the plurality of types of candidate orders. The order determiner 48 determines one selected candidate order as a setting order (S104). As described above, the setting order is the order in which the positional posture of the irradiation nozzle 16 and the treatment table 18 is adapted to each of the plurality of prescribed conditions in the actual treatment.

The display and operation processor 52 displays each prescribed condition on the display device 24 in the setting order determined by the order determiner 48 (S105). While each prescribed condition is displayed, the display and operation processor 52 determines whether or not a display end operation for ending the display of each prescribed condition has been performed in the operation device 22 (S106).

When it is determined that the display end operation is performed, the display and operation processor 52 causes the treatment planning input and output device 42 to execute the process of step S110. The treatment planning input and output device 42 generates a treatment planning TP indicating a finally determined setting order (S110), and transmits the treatment planning TP to the treatment information management device 28. The treatment information management device 28 stores the treatment planning TP. The treatment information management device 28 stores the finally determined setting order by storing the treatment planning TP.

When it is determined that the display end operation is not performed, the display and operation processor 52 determines whether or not the operation device 22 has performed the operation of rearranging the display order of the prescribed conditions (S107).

When it is determined that the display and operation processor 52 has not performed the operation of rearranging the display order of the prescribed conditions, the display and operation processor 52 returns to step S105 and continuously displays each prescribed condition on the display device 24 (S105). When it is determined that the display and operation processor 52 has performed the operation of rearranging the display order of the prescribed conditions, the display and operation processor 52 rearranges the display order and displays the prescribed conditions on the display device 24 (S108).

The setting order changer 50 determines a new setting order according to the rearrangement of the display order of the prescribed conditions (S109). The treatment planning input and output device 42 generates a treatment planning TP indicating a finally determined setting order (S110), and transmits the treatment planning TP to the treatment information management device 28. The treatment information management device 28 stores the treatment planning TP.

Generally, treatment with the particle beam is divided and carried out in a plurality of days. In the treatment on the second and subsequent days, the treatment planning TP is read from the treatment information management device 28 into the control device 20. In the treatment on the second and subsequent days, the setting order is defined by the treatment planning TP, and thus the setting order does not necessarily need to be changed. However, depending on the situation such as the need to change the irradiation direction of the particle beam to the affected area, the same process as the process for the initial treatment planning TP0 may be executed by the control device 20.

(4) Treatment Operation of Particle Beam Therapy Apparatus (4-1) Action by Operator Referring to Display Device While the process illustrated in the flowchart of FIG. 8 is executed, the operator operates the operation device 22 to perform treatment of the affected area. First, the patient is laid down on the treatment table 18. The operator operates the operation device 22 to display the setting order of the plurality of prescribed conditions applied to one type of treatment on the display device 24.

That is, the display and operation processor 52 displays the setting order of the plurality of prescribed conditions applied to one type of treatment on the display device 24 in response to the operation to the operation device 22. The operator refers to the display device 24 and inputs condition designation information for designating the prescribed condition to the operation device 22 for each setup or each irradiation process according to the setting order displayed on the display device 24.

In response to this, the operation device 22 reads the condition designation information. Each time the condition designation information that designates one prescribed condition is read, the position and posture setter 32 adapts the positional posture of the irradiation nozzle 16 and the treatment table 18 to the prescribed conditions designated in the condition designation information.

When the rotation angle position of the irradiation nozzle 16 is made to be adapted to each prescribed condition, the gantry driver 38 changes the rotation angle position of the irradiation nozzle 16 from the previous prescribed condition to the next prescribed condition according to the movement path determined by the movement path determiner 44. When the position and posture of the treatment table 18 are adapted to each prescribed condition, the treatment table driver 34 changes the position and posture of the table 18 from the previous prescribed condition to the next prescribed condition according to the movement path determined by the movement path determiner 44.

The setup is performed when the positional posture of the irradiation nozzle 16 and the treatment table 18 is adapted to the prescribed conditions for setup. Then, the irradiation process is performed when the positional posture of the irradiation nozzle 16 and the treatment table 18 is adapted to the prescribed conditions for the irradiation process. The operator sequentially inputs the condition designation information into the operation device 22 according to the setting order from a first prescribed condition to a last prescribed condition. The position and posture setter 32 adapts the positional posture of the irradiation nozzle 16 and the treatment table 18 to each prescribed condition according to the condition designation information sequentially read by the operation device 22.

(4-2) Semi-Automatic Action According to Setting Order

In this way, instead of the operator checking the setting order according to the display of the display device 24 and the operator inputting the condition designation information in order according to the setting order, the control device 20 may recognize the setting order by itself and execute the process according to the recognition. In this case, the position and posture setter 32 adapts the positional posture of the irradiation nozzle 16 and the treatment table 18 to the prescribed conditions according to the setting order each time a trigger operation is performed by the operation device 22. The trigger operation is an operation for making the positional posture of the irradiation nozzle 16 and the treatment table 18 transition.

In FIG. 9, a flowchart of the treatment action executed by the control device 20 is illustrated. The process illustrated in this flowchart is executed by the operation device 22, the display and operation processor 52, and the position and posture setter 32.

The display and operation processor 52 determines whether or not the trigger operation has been performed by the operation device 22 (S201). The position and posture setter 32 repeats the determination in step S201 while the trigger operation is not performed by the operation device 22. On the other hand, when it is determined that the trigger operation is performed by the operation device 22, the position and posture setter 32 adapts the positional posture of the irradiation nozzle 16 and the treatment table 18 to the prescribed condition according to the setting order (S202).

That is, when the trigger operation is the first time, the position and posture setter 32 adapts the positional posture of the irradiation nozzle 16 and the treatment table 18 to the prescribed condition in which the ranking in the setting order is the first. When the trigger operation is the second time, the position and posture setter 32 adapts positional posture of the irradiation nozzle 16 and the treatment table 18 to the prescribed condition in which the ranking in the setting order is the second. When the trigger operation is the N-th time, the position and posture setter 32 adapts the positional posture of the irradiation nozzle 16 and the treatment table 18 to the prescribed condition in which the ranking in the setting order is the N-th. However, N is an integer of 2 or more.

After step S202 is executed, the position and posture setter 32 determines whether or not the prescribed condition in which the positional posture of the irradiation nozzle 16 and the treatment table 18 is adapted is the last prescribed condition (S203). When it is determined that the prescribed condition is not the last prescribed condition, the position and posture setter 32 returns to the process of step S201. When it is determined that the prescribed condition is the last prescribed condition, the position and posture setter 32 ends the process.

By the process of steps S201 to S203, the position and posture setter 32 makes the positional posture of the irradiation nozzle 16 and the treatment table 18 transition from the first prescribed condition to the last prescribed condition while adapting the positional posture of the irradiation nozzle 16 and the treatment table 18 to each prescribed condition.

(5) Particle Beam Therapy Apparatus with Freely Adjustable Relative Position and Posture In the description above, the embodiment in which the rotation angle position of the irradiation nozzle 16 and the position and posture of the treatment table 18 are freely adjustable has been described. In this way, in addition to the configuration in which the positions and postures of both the irradiation nozzle and the treatment table are freely adjustable, a configuration in which the position and posture of only one of the irradiation nozzle and the treatment table are freely adjustable may be used. Only the position or posture of one of the irradiation nozzle and the treatment table may be freely adjustable, and the position and posture of the other may be freely adjustable.

In this way, in the particle beam therapy apparatus, the relationship between the relative positions and postures of the irradiation nozzle and the treatment table is freely adjustable. In the following description, the relationship between the relative positions and postures of the irradiation nozzle and the treatment table is referred to as "relative position and posture". The relative position and posture is represented, for example, by the position and posture of one of the irradiation nozzle and the treatment table in a coordinate system fixed to the other thereof.

The relative position and posture of the irradiation nozzle and the treatment table can be adjusted by changing the position and posture of one of the irradiation nozzle and the treatment table and the position and posture of the other thereof. When one of the irradiation nozzle and the treatment table is fixed, the relative position and posture can be adjusted by changing the position and posture of the other of the irradiation nozzle and the treatment table. When the position or posture of one of the irradiation nozzle and the treatment table is fixed, the relative position and posture can be adjusted by changing the posture or position of one of the irradiation nozzle and the treatment table and the position and posture of the other thereof.

(6) Second Embodiment

In FIG. 10, a particle beam therapy apparatus 2 according to a second embodiment of the present invention is schematically illustrated. The same components as those illustrated in FIG. 1 are denoted by the same reference numerals. In the particle beam therapy apparatus 2, the irradiation nozzle 16 is fixed to a wall 62. On the other hand, the position and posture of the treatment table 18 are freely adjustable. The irradiation nozzle 16 irradiates the particle beam in the lateral direction when viewed from the operator.

When treating a patient, the treatment table 18 is moved to a position which is irradiated with radiation from the irradiation nozzle 16. After that, the posture of the treatment table 18 is adjusted, and the affected area is irradiated with particle beams from various directions. The control device 200 is a device in which the gantry driver 38 is removed from the control device 20 illustrated in FIG. 2.

(7) Summary of Embodiments

As described above, the particle beam therapy apparatus according to the embodiments of the present invention includes the irradiation nozzle 16 for irradiating the particle beam, the treatment table 18 on which the patient is placed, and the control device 20 or 200 that controls the actions of the irradiation nozzle 16 and the treatment table 18. Each component included in the control device 20 or 200 acts as follows. The position and posture setter 32 moves a movable body that is at least one of the irradiation nozzle 16 and the treatment table 18 which are capable of motion, and sets the relative position and posture of the irradiation nozzle 16 and the treatment table 18.

The movement path determiner 44 determines the movement path of the movable body when the positional posture of the movable body is adapted from one condition among a plurality of prescribed conditions to another condition. The positional posture of the movable body is defined as at least one of the position and posture of the movable body. The movement path determiner 44 may determine the movement path of the movable body between the plurality of prescribed conditions. The information indicating the movement path may include a geometric quantity representing a change in posture of the treatment table 18 when the position of the treatment table 18 is constant. Depending on the embodiment, the information indicating the movement path may include a geometric quantity representing a change in posture of the irradiation nozzle 16 when the position of the irradiation nozzle 16 is constant.

The evaluation value determiner 46 obtains an evaluation value when the positional posture of the movable body is adapted to each of the plurality of prescribed conditions. This evaluation value represents the motion state of the movable body when the movable body is moved according to the movement path and one type of treatment is performed. The order determiner 48 determines the setting order for adapting the positional posture of the movable body to each of the plurality of prescribed conditions based on the evaluation value.

In one type of treatment, the position and posture setter 32 moves the movable body according to the movement path determined by the movement path determiner 44 and adapts the positional posture of the movable body from one condition among the plurality of prescribed conditions condition to another condition.

The particle beam therapy apparatus according to each embodiment of the present invention uses a control method established by the following matters (i) to (vi). The control device 20 or 200 may execute a control program that executes this control method.

(i) By the movement path determiner 44, the movement path of the movable body when adapting the positional posture of the movable body from one condition among a plurality of prescribed conditions to another condition is determined.

(ii) By the evaluation value determiner 46, an evaluation value for a case of adapting the positional posture of the movable body to each of the plurality of prescribed conditions by moving the movable body according to the movement path is obtained.

(iii) By the order determiner 48, the setting order for adapting the positional posture of the movable body to each of the plurality of prescribed conditions is determined based on the evaluation value.

(iv) In one type of treatment, by the position and posture setter 32, the positional posture of the movable body is adapted from one condition among a plurality of specified conditions to another condition by moving the movable body according to the movement path described above.

(8) Effect

According to the particle beam therapy apparatus according to this embodiment, the setting order for the positional posture of the movable body is determined based on the evaluation value. Accordingly, the operator does not need to empirically determine the setting order while referring to the treatment planning. With this configuration, the burden on the operator is reduced.

According to the particle beam therapy apparatus according to this embodiment, the information indicating the setting order and the evaluation value are displayed on the display device 24. Accordingly, a validity of the determined setting order is indicated by the evaluation value.

When the evaluation value is the movement time of the movable body in one type of treatment, the following effects can be obtained. That is, physical stress or mental stress given to the patient is reduced by determining the setting order so that the evaluation value becomes an appropriate value (for example, the minimum value). Furthermore, the time required for treatment is reduced.

When the evaluation value is the work given to the moving body in one type of treatment, the following effects can be obtained. That is, electric energy consumed by the particle beam therapy apparatus is reduced by determining the setting order so that the evaluation value becomes an appropriate value (for example, the minimum value).

When the evaluation value is a motion load given to the treatment table 18 in one type of treatment, the following effects can be obtained. That is, physical stress or mental stress given to the patient is reduced by determining the setting order so that the evaluation value becomes an appropriate value (for example, the minimum value).

By the configuration in which the evaluation value is displayed on the display device 24 together with the setting order and the setting order is changed by the operation on the operation device 22, the following effects can be obtained. That is, the setting order can be determined based not only on the evaluation value but also on the operation of the operator. When the setting order is regularly determined by the evaluation value, it may be difficult to perform an action for checking the action or an appropriate action according to the treatment situation. According to this embodiment, the action of the movable body according to an irregular situation can be performed by the operation of the operator.

The movement path of the movable body is required so that the irradiation nozzle 16 and the patient do not come into contact with each other, or the irradiation nozzle 16 and the treatment table 18 do not come into contact with each other. Alternatively, the movement path of the movable body is required so that the irradiation nozzle 16 and the patient do not come into contact with each other and the irradiation nozzle 16 and the treatment table 18 do not come into contact with each other. With this configuration, safety during treatment is ensured.

(9) Application Embodiments

The application embodiments for the embodiments described above are described below. Each application embodiment is an application of the first embodiment. In the first embodiment, the prescribed condition determines the rotation angle position of the irradiation nozzle 16 and the position and posture of the treatment table 18. By using the prescribed conditions for determining the position and posture of the treatment table 18, a similar application embodiment is established for the second embodiment.

In FIG. 11, an example of the prescribed conditions defined by the initial treatment planning TP0 is illustrated. In this example, by the initial treatment planning TP0, one prescribed condition Stp1 for setup and three prescribed conditions Tx1 to Tx3 for the irradiation process are defined. Unlike the example illustrated in FIG. 3, the prescribed condition Stp1 and the prescribed conditions Tx1 to Tx3 individually determine the rotation angle position of the irradiation nozzle 16. The prescribed condition Stp1 and the prescribed conditions Tx1 to Tx3 individually determine the position and posture of the treatment table 18.

For the rotating gantry 14, the rotation angle position thereof is determined by each prescribed condition. For the treatment table 18, the position and posture thereof are determined by each prescribed condition. For simplicity of notation, in FIG. 11, only the yaw angle is illustrated as one quantity representing the posture thereof.

By the prescribed condition Stp1, an angle of 0° is set to the rotation angle position of the rotating gantry 14. By the prescribed condition Tx1, the rotation angle position of the rotating gantry 14 is set to 180°. By the prescribed condition Tx2, the rotation angle position of the rotating gantry 14 is set to 60°. By the prescribed condition Tx3, the rotation angle position of the rotating gantry 14 is set to 90°.

By the prescribed condition Stp1, the yaw angle of the treatment table 18 is set to 270°. By the prescribed condition Tx1, the yaw angle of the treatment table 18 is set to 180°. By the prescribed condition Tx2, the yaw angle of the treatment table 18 is set to 0°. By the prescribed condition Tx3, the yaw angle of the treatment table 18 is set to 180°.

In FIG. 12, the setting order in which the movement time as the evaluation value is minimized is conceptually illustrated. The order in which the positional posture of the irradiation nozzle 16 and the treatment table 18 transitions is indicated by solid arrows. In this setting order, the positional posture of the irradiation nozzle 16 and the treatment table 18 transitions in the order of the start condition Start, the prescribed condition Stp1, the prescribed condition Tx3, the prescribed condition Txi, the prescribed condition Tx2, and the prescribed condition Start.

In FIG. 13, an example of an image illustrated on the display device 24 is illustrated. The same items as those illustrated in FIG. 6 are denoted by the same reference numerals. The setting order display unit 56 includes a field indicating designated ranking in addition to the fields for displaying the prescribed condition, the rotation angle position of the rotating gantry 14, and the yaw angle of the treatment table 18.

The specific numerical values of the rotation angle positions of the rotating gantry 14 associated with the respective prescribed conditions Stpi and Txi are the same as those in FIG. 11. The specific numerical values of the yaw angles of the treatment table 18 associated with the respective prescribed conditions Stpi and Txi are the same as those in FIG. 11.

On the display screen 54, the prescribed conditions are illustrated in the setting order determined first. The ranking of the prescribed condition Stp1 is the first, and the ranking of the prescribed condition Tx3 is the second. The ranking of the prescribed condition Tx1 is the third, and the ranking of the prescribed condition Tx2 is the fourth.

On this display screen 54, an operation of changing the setting order by the operator is performed. In the field for entering the designated ranking, a numerical value indicating the ranking to be occupied by the prescribed condition associated with the field in the changed setting order is input.

The display screen 54 includes a recalculation button 64. As illustrated in the upper side of FIG. 14, the designated ranking is input in the field of designated ranking by the operation of the operator. In the example shown on the upper side of FIG. 14, 1 is input as the designated ranking for the prescribed condition Stp1, and 2 is input as the designated ranking for the prescribed condition Tx1.

When the recalculation button 64 is pressed by the cursor based on the operation of the operator after the designated ranking is input, a new setting order is determined. The new setting order is determined based on the evaluation value under a constraint condition that the ranking of the prescribed condition Stp1 is fixed to the first and the ranking of the prescribed condition Tx1 is fixed to the second. That is, among the plurality of candidate orders, the new setting order is selected from the one in which the ranking of the prescribed condition Stp1 is the first and the ranking of the specified prescribed Tx1 is the second. This selection is made based on the evaluation value corresponding to the candidate order.

On the display screen 54 illustrated on the lower side of FIG. 14, the prescribed conditions are illustrated in the new setting order after the change. The ranking of the prescribed condition Stp1 is the first, and the ranking of the prescribed condition Tx1 is the second. The ranking of the prescribed condition Tx3 is the third, and the ranking of the prescribed condition Tx2 is the fourth. The movement time is illustrated on the evaluation value display unit 60 as the evaluation value for the new setting order.

The process of changing the setting order based on the designated ranking is executed by the operation device 22, the display and operation processor 52, the setting order changer 50, the display device 24, and the treatment planning input and output device 42. The display and operation processor 52 recognizes the operation performed by the operation device 22. The display and operation processor 52 displays the image illustrated in FIG. 13 on the display device 24 in response to the operation performed to the operation device 22. When the designated ranking is input on the display screen 54 by the operation on the operation device 22 and the recalculation button 64 is pressed, the display and operation processor 52 reads the designated ranking.

The setting order changer 50 changes the setting order according to the designated ranking being read. That is, the setting order changer 50 selects the one in which the prescribed condition (constraint prescribed condition), in which the ranking is designated, occupies the designated ranking among the plurality of candidate orders as the new setting order. The setting order changer 50 selects the new setting order based on the evaluation value corresponding to the candidate order.

As illustrated on the lower side of FIG. 14, the display and operation processor 52 displays the prescribed conditions on the display device 24 in the new setting order after the change. The display and operation processor 52 further displays the evaluation value obtained for the new setting order after the change on the display device 24.

The treatment planning input and output device 42 generates a treatment planning TP indicating a finally determined setting order, and transmits the treatment planning TP to the treatment information management device 28. The treatment information management device 28 stores the treatment planning TP.

In this way, when there is a constraint prescribed condition among the plurality of prescribed conditions, the setting order changer 50 determines the setting order as follows. That is, the setting order changer 50 determines the one, in which the ranking of the constraint prescribed condition is the designated ranking, among the plurality of types of orders for adapting the positional posture to each of the plurality of prescribed conditions, as the new setting order.

Here, an example in which the designated ranking as a constraint condition is input by the operator is indicated. As another example, the designated ranking may be predetermined for a specific prescribed condition. For example, regarding the prescribed conditions for setup, the designated ranking may be set as the first.

According to this application embodiment, the following effects can be obtained. That is, it may be necessary to designate ranking of the prescribed conditions in an action for checking the action and the like. Depending on the treatment situation, it is desirable to rank the specific prescribed condition higher. According to this application embodiment, the irradiation nozzle 16 and the treatment table 18 can act according to an irregular situation by designating ranking of specific prescribed conditions.

An application embodiment in which a course of treatment can be referenced by the operator is described below. In FIG. 15, an image displayed on the display device 24 is illustrated. The same items as those illustrated in FIGS. 6, 7, 13, and 14 are denoted by the same reference numerals.

Generally, treatment with the particle beam therapy apparatus is divided and carried out in a plurality of days. On the display screen 54, tab parts 66 corresponding to the number of days that the treatment has been performed so far and the number of days that the treatment will be performed from now on are displayed.

In FIG. 15, the display screen 54 when the treatment for two days has already been performed and the treatment for the third day is performed is illustrated. Each treatment planning TP generated according to the treatment so far is stored in the treatment information management device 28. When the treatment is started, the control device 20 reads the treatment planning TP generated by the treatment so far from the treatment information management device 28. The operator operates the tab part 66 as necessary to display the setting order in the treatment performed in the past on the display device 24.

The process of displaying the display screen 54 illustrated in FIG. 15 on the display device 24 is executed by the operation device 22, the treatment planning input and output device 42, the display and operation processor 52, and the display device 24. The display and operation processor 52 recognizes the operation performed by the operation device 22. When an operation of clicking the tab part 66 displayed on the display device 24 with the cursor is performed in the operation device 22, the treatment planning input and output device 42 reads the treatment planning TP corresponding to the clicked tab part 66 from the treatment information management device 28. The display and operation processor 52 displays the treatment planning TP read by the treatment planning input and output device 42 on the display device 24.

According to this embodiment, the setting order in the treatment performed in the past is indicated to the operator. With this configuration, a judgment material when determining the setting order in the next treatment is indicated to the operator.

In the description above, an example of displaying the past setting order by clicking the tab part 66 is indicated. In addition to the tab part 66, the past setting order may be displayed on the display screen 54 by clicking an icon, a button, or the like.

REFERENCE SIGNS LIST 1, 2, 100: particle beam therapy apparatus
10: accelerator
12: beam transport device
14, 106: rotating gantry
16, 104: irradiation nozzle
18, 102: treatment table
20: control device
22: operation device
24: display device
26: treatment planning device
28: treatment information management device
30: memory
32: position and posture setter
34: treatment table driver
36, 40: drive circuit
38: gantry driver
42: treatment planning input and output device
44: movement path determiner
46: evaluation value determiner
48: order determiner
50: setting order changer
52: display and operation processor
54: display screen
56: setting order display unit
58: edit button
60: evaluation value display unit
62: wall
64: recalculation button
66: tab part
108: particle beam
Tp0: initial treatment planning
Tp: treatment planning

The invention claimed is:

1. A particle beam therapy apparatus comprising:
an irradiation nozzle that irradiates a particle beam;
a treatment table on which a patient is placed; and
a control device that moves a movable body and sets a relative position and posture of the irradiation nozzle and the treatment table, the movable body being at least one of the irradiation nozzle and the treatment table that is capable of motion,
wherein the control device:
determines a movement path of the movable body when adapting the positional posture of the movable body from one condition among a plurality of prescribed conditions to another condition of a treatment,
obtains an evaluation value for each of a plurality of candidate orders, each candidate order indicating a different series of positional postures of moving the moveable body according to each of the plurality of prescribed conditions of the treatment, each evaluation value representing a motion state of the moving body upon moving the moving body according to the movement path to each positional posture of each prescribed condition,
determines a setting order for adapting the positional posture of the movable body to each of the plurality of prescribed conditions based on the evaluation values of each candidate order, and
adapts the positional posture of the movable body from one condition among the plurality of prescribed conditions to another condition by moving the movable body according to the movement path of the setting order.

2. The particle beam therapy apparatus according to claim 1,
wherein the evaluation value is a movement time of the movable body when the one type of treatment is performed.

3. The particle beam therapy apparatus according to claim 2,
wherein the control device determines an order, in which the evaluation value is minimized, among the plurality candidate orders for adapting the positional posture of the movable body to each of the plurality of prescribed conditions, as the setting order.

4. The particle beam therapy apparatus according to claim 2, further comprising:
a display device, coupled to the control device, that displays information indicating the setting order and the evaluation value.

5. The particle beam therapy apparatus according to claim 1,
wherein the movable body is the treatment table, and
wherein the evaluation value indicates a motion load applied to the movable body when the one type of treatment is performed.

6. The particle beam therapy apparatus according to claim 5,
wherein the control device determines an order, in which the evaluation value is minimized, among the candidate orders for adapting the positional posture of the movable body to each of the plurality of prescribed conditions, as the setting order.

7. The particle beam therapy apparatus according to claim 5, further comprising:
a display device, coupled to the control device, that displays information indicating the setting order and the evaluation value.

8. The particle beam therapy apparatus according to claim 1, further comprising:
a display device, coupled to the control device, that displays information indicating the setting order and the evaluation value.

9. The particle beam therapy apparatus according to claim 1, further comprising:
a display device, coupled to the control device, that displays information indicating the setting order,
wherein the control device changes the setting order according to read operation information while information indicating the setting order is displayed.

10. The particle beam therapy apparatus according to claim 9,
wherein the display device displays the evaluation value for the setting order after the change.

11. The particle beam therapy apparatus according to claim 1,
wherein when a constraint prescribed condition in which ranking for adapting the positional posture of the movable body is designated is present among the plurality of prescribed conditions, the control device determines the order, in which the ranking of the constraint prescribed condition is designated ranking, among a plurality of candidate orders for adapting the positional posture of the movable body to each of the plurality of prescribed conditions as the setting order.

12. The particle beam therapy apparatus according to claim 1,
wherein the control device determines the movement path so that the irradiation nozzle does not come into contact with the treatment table or the patient.

13. A control method of a particle beam therapy apparatus which includes an irradiation nozzle for irradiating a particle beam and a treatment table on which a patient is placed and moves a movable body and sets a relative position and posture of the irradiation nozzle and the treatment table, the movable body being at least one of the irradiation nozzle and the treatment table that is capable of motion, the control method comprising:
determining a movement path of the movable body when adapting the positional posture of the movable body from one condition among a plurality of prescribed conditions to another condition of a treatment;
obtaining an evaluation value for each of a plurality of candidate orders, each candidate order indicating a different series of positional postures of moving the moveable body according to each of the plurality of prescribed conditions of the treatment, each evaluation value representing a motion state of the moving body upon moving the moving body according to the movement path to each positional posture of each prescribed condition;
determining a setting order for adapting the positional posture of the movable body to each of the plurality of prescribed conditions based on the evaluation value values of each candidate order; and
adapting the positional posture of the movable body from one condition among the plurality of prescribed conditions to another condition by moving the movable body according to the movement path of the setting order.

* * * * *